United States Patent
Endo et al.

(10) Patent No.: US 6,617,424 B2
(45) Date of Patent: Sep. 9, 2003

(54) UNDECAPEPTIDES CONTAINING CYSTEINESULFINIC AND CYSTEINESULFENIC ACID

(75) Inventors: Isao Endo, Kokubunji (JP); Masafumi Odaka, Wako (JP); Masafumi Yohda, Wako (JP); Masayoshi Nakasako, Wako (JP); Koji Takio, Wako (JP)

(73) Assignee: The Institute of Physical and Chemical Research, Wako (JP)

( * ) Notice: Subject to any disclaimer, the term of this patent is extended or adjusted under 35 U.S.C. 154(b) by 0 days.

(21) Appl. No.: 09/805,548

(22) Filed: Mar. 14, 2001

(65) Prior Publication Data

US 2002/0037996 A1 Mar. 28, 2002

Related U.S. Application Data

(62) Division of application No. 09/113,312, filed on Jul. 10, 1998, now Pat. No. 6,268,475.

(30) Foreign Application Priority Data

Jul. 11, 1997 (JP) .............................................. 9-187026
Apr. 7, 1998 (JP) .............................................. 10-94296

(51) Int. Cl.[7] .............................................. C07K 7/06
(52) U.S. Cl. ..................................................... 530/327
(58) Field of Search ......................................... 530/327

(56) References Cited

U.S. PATENT DOCUMENTS 5,089,411 A * 2/1992 Yamada et al. .............. 435/129

OTHER PUBLICATIONS

Nagashima et al. "Novel Non–Heme Iron Center of Nitrile Hydratase with a Claw Setting of Oxygen Atoms" (May, 1998) Nat. Struct. Biol., 5(5), 347–351.*

Tsujimura et al., "Structure of the Photoreactive Iron Center of the Nitrile Hydratase from Rhodococcus sp. N–771" (Nov. 1997) J. Biol. Chem., 272(47), 29454–29459.*

Dugas et al., "Bioinorganic Chemistry, A Chemical Approach to Enzyme Action" (1981) Springer–Verlag, New York.*

Odaka et al., "Activity Regulation of Photoreactive Nitrile Hydratase by Nitric Oxide" (1997) J. Am. Chem. Soc., 119(16), 3785–3791.*

Odaka, et al., Journal of the American Chemical Society, "Activity Regulation of Photoreactive Nitrile Hydratase by Nitric Oxide", vol. 119, No. 16, pp. 3785–3791, 1997.

Nagashima et al, "Novel Non–Heme Iron Center of Nitrile Hydratase with a Claw Setting of Oxygen Atoms", Nat. Struct. Biol., 5(5), pp. 347–351 (May 1998).

Tsujimura et al., "Structure of the Photoreactive Iron Center of the Nitrile Hydratase from Rhodococcus sp. N–771", J. Biol. Chem., 272(47), 29454–29459 (Nov. 1997).

Dugas et al., "Bioinorganic Chemistry, a Chemical Approach to Enzyme Action", Springer–Verlag, New York. (1981).

* cited by examiner

Primary Examiner—Jon P. Weber
(74) Attorney, Agent, or Firm—Burns, Doane, Swecker & Mathis, L.L.P.

(57) ABSTRACT

Disclosed are peptides represented by $IVC_1SLC_2SC_3TAW$ and $C_1SLC_2SC_3$ wherein I stands for isoleucine, V for valine, $C_1$ for cysteine, $C_2$ for cysteinesulfinic acid, $C_3$ for cysteinesulfenic acid, S for serine, L for leucine, T for threonine, A for alanine, and W for tryptophan. These peptides can impart photoreactivity to a protein by binding to a non-heme iron. Also disclosed are methods for imparting photoreactivity to cells by introducing the peptide sequences into at least one protein which is involved in a metabolic system and/or energy metabolic system of the cells. There can be provided peptide sequences with a shorter peptide chain capable of imparting photoreactivity, which can be easily introduced into a protein with a little risk in degrading original function of the protein. There are also provided methods enabling control of metabolic reactions by imparting photoreactivity to cells with the peptides.

3 Claims, 7 Drawing Sheets

SEQUENCE LISTING

<160> NUMBER OF SEQ ID NOS: 6

<210> SEQ ID NO 1
<211> LENGTH: 10
<212> TYPE: PRT
<213> ORGANISM: Rhodococcus sp. N-771

```
<220> FEATURE:
<221> NAME/KEY: PEPTIDE
<222> LOCATION: (5)
<223> OTHER INFORMATION: Amino acid at position 5 is Xaa wherein Xaa =
      an arbitrary amino acid.

<400> SEQUENCE: 1

Ile Val Cys Leu Xaa Ser Cys Thr Ala Trp
 1               5                  10

<210> SEQ ID NO 2
<211> LENGTH: 5
<212> TYPE: PRT
<213> ORGANISM: Rhodococcus sp. N-771
<220> FEATURE:
<221> NAME/KEY: PEPTIDE
<222> LOCATION: (3)
<223> OTHER INFORMATION: Amino acid at position 3 is Xaa wherein Xaa =
      an arbitrary amino acid.

<400> SEQUENCE: 2

Cys Leu Xaa Ser Cys
 1               5

<210> SEQ ID NO 3
<211> LENGTH: 11
<212> TYPE: PRT
<213> ORGANISM: Rhodococcus sp. N-771
<220> FEATURE:
<221> NAME/KEY: PEPTIDE
<222> LOCATION: (1)..(11)
<223> OTHER INFORMATION: Amino acids at positions 1, 2, 4, 5, 9, 10 & 11
      are Xaa wherein Xaa = an arbitrary amino acid.
<221> NAME/KEY: PEPTIDE
<222> LOCATION: (6)..(8)
<223> OTHER INFORMATION: Amino acid at position 6 is Xaa wherein Xaa =
      cysteinesulfinic acid.
<221> NAME/KEY: PEPTIDE
<222> LOCATION: (6)..(8)
<223> OTHER INFORMATION: Amino acid at position 8 is Xaa wherein Xaa =
      cysteinesulfenic acid.

<400> SEQUENCE: 3

Xaa Xaa Cys Xaa Xaa Xaa Ser Xaa Xaa Xaa Xaa
 1               5                  10

<210> SEQ ID NO 4
<211> LENGTH: 11
<212> TYPE: PRT
<213> ORGANISM: Rhodococcus sp. N-771
<220> FEATURE:
<221> NAME/KEY: PEPTIDE
<222> LOCATION: (1)..(11)
<223> OTHER INFORMATION: Amino acid at position 6 is Xaa wherein Xaa =
      cysteinesulfinic acid.
<221> NAME/KEY: PEPTIDE
<222> LOCATION: (1)..(11)
<223> OTHER INFORMATION: Amino acid at position 8 is Xaa wherein Xaa =
      cysteinesulfenic acid.

<400> SEQUENCE: 4

Ile Val Cys Ser Leu Xaa Ser Xaa Thr Ala Trp
 1               5                  10

<210> SEQ ID NO 5
<211> LENGTH: 21
<212> TYPE: PRT
<213> ORGANISM: Rhodococcus sp. N-771

<400> SEQUENCE: 5
```

```
Asn Val Ile Val Cys Ser Cys Thr Ala Trp Pro Ile Leu Gly Leu Pro
 1               5                  10                  15

Pro Thr Trp Tyr Lys
             20

<210> SEQ ID NO 6
<211> LENGTH: 10
<212> TYPE: PRT
<213> ORGANISM: Rhodococcus sp. N-771

<400> SEQUENCE: 6

Ile Val Ser Leu Cys Ser Cys Thr Ala Trp
 1               5                  10
```

UNDECAPEPTIDES CONTAINING CYSTEINESULFINIC AND CYSTEINESULFENIC ACID

This a divisional of application Ser. No. 09/113,312, filed Jul. 10, 1998, now U.S. Pat. No. 6,268,475.

FIELD OF THE INVENTION

The present invention relates to a peptide which can impart photoreactivity to a protein, and a method for controlling metabolism of cells by introducing a sequence of the peptide into at least one protein which functions in a metabolic system so that the protein should acquire photoreactivity, thereby controlling metabolism of cells.

BACKGROUND OF THE INVENTION

Nitrile hydratase (NHase) is an enzyme which is produced in microorganisms and converts a nitrile compound into an amide compound by hydration. It is a soluble metalloprotein containing iron or cobalt atom in its active center. NHase derived from Rhodococcus sp. N-771 strain has a non-heme iron center of mononuclear low-spin six coordinate Fe(III). NHases have been isolated from several kinds of bacterial cells, and all of them consist of two kinds of subunits, α and β. Both of the subunits have a molecular weight of about 23,000. NHases of Rhodococcus sp. N-771, N-774, and R312 are considered to be the same enzyme because their base sequences are identical to each another, and their enzymatic activity varies with light irradiation. Namely, when bacterial cells exhibiting high activity are left in the dark, the enzyme activity is reduced, and the activity is increased again by photo-irradiation.

It was recently revealed that photodissociation of nitric oxide (NO) which is bound to the non-heme iron center of inactive form Nhase activates the enzyme (Odaka et al., J. Am. Chem. Soc., 119, 3785–3791 (1997)). However, because the structure of the non-heme iron center which is the photoreactive site was not elucidated yet, the detailed mechanism of the photoreaction remained unclear. Therefore, the present inventors performed structural analysis of the non-heme iron center, and reported the results (for example, see Protein, Nucleic acid, Enzyme, Vol.42, No.2, p38–45 (1997)). That is, the present inventor isolated the α and β subunits from the inactive form enzyme under denaturation condition, and found that the NO-binding type non-heme iron center is present on the α subunit. Therefore, they further performed enzymatic degradation of the α subunit with trypsin, and purified the resulting peptides by reversed phase chromatography under a neutral condition. As a result, a peptide consisting of 24 residues of $_{105}$N to $_{128}$K binding one iron atom and NO has been isolated. This region was well conserved in various kinds of NHases, and contained a cysteine cluster predicted to be a metal-binding site ($_{109}$C-S-L-$_{112}$C-S-$_{114}$C).

By the way, development of processes for producing useful biomolecules such as amino acids, peptides, proteins, carbohydrates, lipids and the like by utilizing metabolic systems of cells including energy metabolic systems has been performed for a long time. However, in conventional metabolically controlled fermentation, fermentation system for the objective product is constructed through trials on screening and concentration of variants resistant to an analogue having a structure analogous to an objective product. Further, to control the constructed fermentation system, physical factors such as pH and temperature and chemical factors such as substrate concentration and addition of inducers must be changed. Therefore, various regulatory mechanisms of the living body are often affected, and many parameters must be determined for optimization of the production scheme. Moreover, regulatory methods of this type have a drawback that it takes a long period of time to obtain a reaction to stimulation. Therefore, if it is possible construct a method for controlling metabolism which enables proper turning on and turning off a desired intracellular metabolic system so as to produce a desired product in a necessary amount when it is required, it will greatly contribute to fermentation processes.

Accordingly, the present inventors studied out a method for artificially controlling metabolism of cells including energy metabolism by utilizing the peptide stably binding a non-heme iron, which is the photoreactive site of NHase mentioned above. That is, such a peptide as mentioned above is introduced into a protein which functions in a metabolic system of an objective product to impart photoreactivity to the protein so that the metabolic system can be controlled by presence or absence of light irradiation. In this method, photo-control of activity is realized by modifying a protein which functions in a specific reaction system in a metabolic pathway of an objective product. Because the protein to be modified can be arbitrarily selected depending on the purpose, the method has advantages that the screening step by trial and error like in the conventional method does not required, and that fermentation system of which metabolism is controlled can be precisely constructed. Furthermore, because activation of enzyme is achieved by photostimulation, fermentation operation can be performed more simply and quickly compared with the conventional methods.

However, when such a peptide sequence as mentioned above is introduced into various kinds of proteins working in intracellular substance metabolic systems or energy metabolic systems to impart photoreactivity to the metabolism or the energy metabolism, a relatively large peptide like the aforementioned peptide of 24 residues might have problems. The problems are that efficient reaction could not be obtained, or introduction of the peptide impairs the original function of the labeled protein in high possibility, because the relatively large protein contains a large fraction of sequence other than the minimum portion essential for the photoreaction.

SUMMARY OF THE INVENTION

Therefore, the object of the present invention is to provide a peptide sequence capable of efficient photoreaction, which is a peptide chain of a minimum unit capable of imparting photoreactivity, not likely to impair an original function of a labeled protein, and a method for enabling control of metabolic reaction by utilizing the peptide to impart photoreactivity to cells.

The present invention relates to a peptide having a sequence [SEQ ID NO:3] represented by the following general formula (1).

$$X_1X_2C_1X_3X_4C_2SC_3X_5X_6X_7 \qquad (1)$$

wherein $X_1$ to $X_7$ represents an arbitrary amino acid, $C_1$ represents cysteine, $C_2$ represents cysteinesulfinic acid, $C_3$ represents cysteinesulfenic acid, and S represents serine.

An embodiment of the present invention is the aforementioned peptide wherein the sequence [SEQ ID NO:4] represented by the general formula (1) is represented as IVC$_1$SLC$_2$SC$_3$TAW wherein I represents isoleucine, V represents valine, C$_1$ represents cysteine, C$_2$ represents cysteinesulfinic acid, $C_3$ represents cysteinesulfenic acid, S represents serine, L represents leucine, T represents threonine, A represents alanine, and W represents tryptophan.

Another embodiment of the present invention is the aforementioned peptide wherein $X_1$ to $X_7$ in the sequence represented by the general formula (1) are selected from amino acids which can maintain higher order structure of a peptide represented by $IVC_1SLC_2SC_3TAW$ in nitrile hydratase derived from Rhodococcus sp.N-771.

A further embodiment of the present invention is a peptide having a sequence represented by the following general formula (2):

$$C_1X_3X_4C_2SC_3 \qquad (2)$$

wherein $X_3$ and $X_4$ represent arbitrary amino acids, $C_1$ represents cysteine, $C_2$ represents cysteinesulfinic acid, $C_3$ represents cysteinesulfenic acid, and S represents serine. Examples of the above peptide include, for example, the aforementioned peptide wherein the sequence represented by the general formula (2) is represented as $C_1SLC_2SC_3$ wherein $C_1$ represents cysteine, $C_2$ represents cysteinesulfinic acid, $C_3$ represents cysteinesulfenic acid, S represents serine, and L represents leucine. Examples of the above peptide further include, for example, the aforementioned peptide wherein $X_3$ and $X_4$ in the sequence represented by the general formula (2) are selected from amino acids which can maintain higher order structure of a peptide represented by $C_1SLC_2SC_3$ in nitrile hydratase derived from Rhodococcus sp. N-771.

The peptides of the present invention can be a peptide which can impart photoreactivity to a protein by binding a non-heme iron, or a peptide which can form a claw setting structure by binding a non-heme iron.

The present invention also relates to a method for imparting photoreactivity to a cell by introducing one of the aforementioned peptide sequences of the present invention into at least one protein which is involved in a metabolic system and/or energy metabolic system of the cell.

In the method of the present invention, together with the peptide sequence, a non-heme iron binding to the peptide can be introduced.

The present invention also relates to a cell having an NO producing system and photoreactivity wherein one of the aforementioned peptide sequences of the present invention is introduced into at least one protein which is involved in a metabolic system and/or energy metabolic system of the cell.

The cell of the present invention may be, for example, a cell introduced with the peptide sequence and a non-heme iron binding to the peptide, or a cell wherein the peptide sequence and the non-heme iron form a claw setting structure.

DETAILED DESCRIPTION OF THE INVENTION

Figure 1:
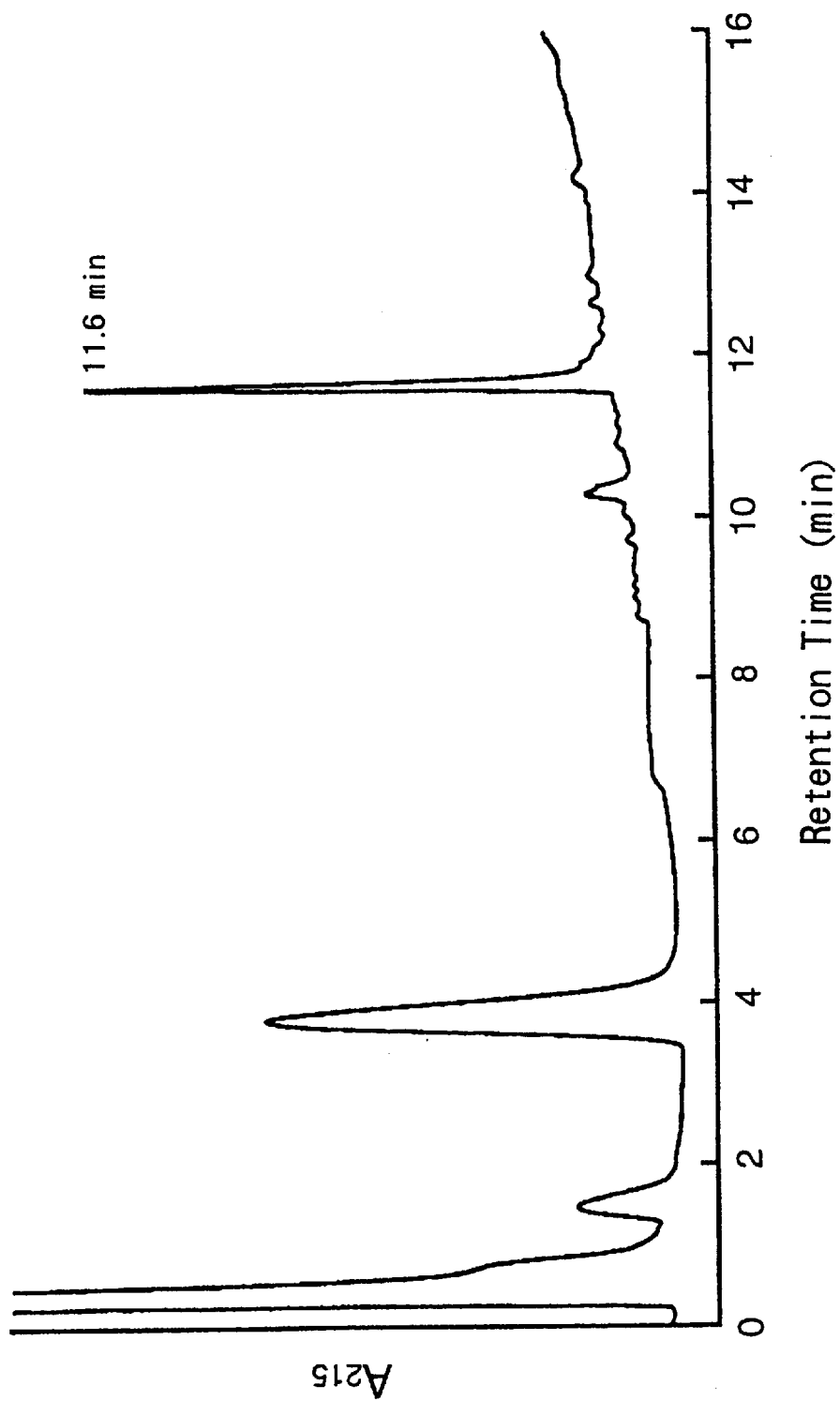
FIG. 1 represents results of reverse phase HPLC of products from digestion with thermolysin, carboxypeptidase-Y and leucine aminopeptidase-M.

As described above, by enzymatically degrading with trypsin the $\alpha$ subunit of NHase having photoreactivity similar to that of wild type NHase and binding an NO-binding type non-heme iron center, a peptide complex consisting of 24 residues of $_{105}N$ to $_{128}K$ which is binding one iron atom and NO per one peptide can be isolated. The present inventors further digested the above peptide of 24 residues with thermolysin, leucine aminopeptidase-M and carboxypeptidase-Y, and found a peptide which is composed of 11 residues, forms a stable complex with a non-heme iron, and is a minimum unit for imparting photoreactivity. This peptide is a peptide represented as $IVC_1SLC_2SC_3TAW$ wherein I represents isoleucine, V represents valine, $C_1$ represents cysteine, $C_2$ represents cysteinesulfinic acid, $C_3$ represents cysteinesulfenic acid, S represents serine, L represents leucine, T represents threonine, A represents alanine, and W represents tryptophan.

The present inventors further examined the structure of the active center of the above peptide by X-ray crystallographic analysis. As a result, it was found that the 6-residue $C_1SLC_2SC_3$ containing $C_1$, $C_2$, S and $C_3$ formed a stable complex directly with the non-heme iron.

Mass spectrometry analysis was performed for the 24-residue peptide in order to obtain its microstructural information. When mass of the peptide was determined under light irradiation, the obtained mass was larger than its theoretical molecular weight by 32 Da. All of the amino acid residues of this sequence except for the three cysteine residues had been determined by analysis with a protein sequencer. Therefore, the peptide was subjected to reduction and then carboxymethylation, and analyzed by the protein sequencer. As a result, only the 112nd cysteine was not carboxymethylated. Therefore, the obtained peptide was subjected to second digestion with thermolysin, and then degraded with aminopeptidase for amino acid analysis. The 112nd cysteine was detected as the same peak as commercially available cysteinesulfinic acid, and thus it was confirmed that this residue existed as sulfinic acid. In contrast, any cysteine residue was not modified in an $\alpha$ subunit which was expressed as a recombinant in E. coli, and it has been revealed that the 112nd cysteine is specifically modified to sulfinic acid in Rhodococcus sp. N-771.

In the aforementioned peptide, $C_3$ represents cysteinesulfenic acid, and it was confirmed that $C_3$ is cysteinesulfenic acid by analysis of the peptide digested with trypsin using Fourier transform ion cyclotron resonance mass spectrometry (FT-ICR MS).

The present invention further relates to a peptide having a sequence represented by the general formula (1). This peptide was defined based on the aforementioned sequence $IVC_1SLC_2SC_3TAW$ with a consideration of the binding of this peptide and iron atom.

$$X_1X_2C_1X_3X_4C_2X_5X_6X_7 \qquad (1)$$

In the formula, $X_1$ to $X_7$ represent arbitrary amino acids, but in particular they are suitably selected from amino acids which can maintain the higher order structure of the above sequence $IVC_1SLC_2SC_3TAW$.

The present invention also relates to a peptide having a sequence represented by the general formula (2). This peptide was defined based on the aforementioned sequence $C_1SLC_2SC_3$ with a consideration of the binding of this peptide and iron atom.

$$C_1X_3X_4C_2SC_3 \quad (2)$$

In the formula, $X_3$ and $X_4$ represent arbitrary amino acids, but in particular they are suitably selected from amino acids which can maintain the higher order structure of the above sequence $C_1SLC_2SC_3$.

Figure 3:
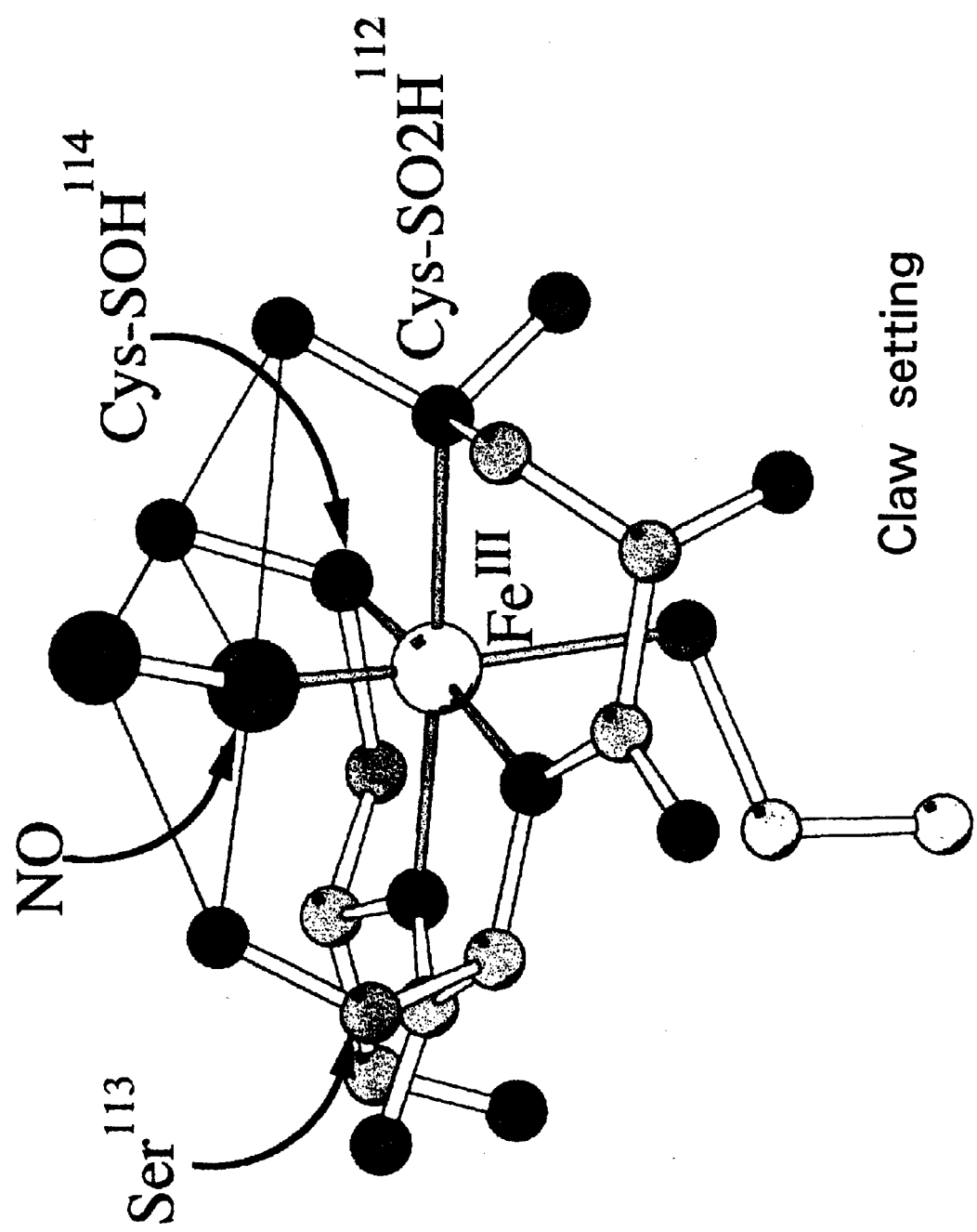
FIG. 3 shows a claw setting structure formed by a peptide $C_1SLC_2SC_3$ binding to a non-heme iron. In this figure, a binding NO molecule is also shown.

In particular, the above sequences $IVC_1SLC_2SC_3TAW$ and $C_1SLC_2SC_3$ are bound to a non-heme iron to form the claw setting structure with it represented in FIG. 3. $C_1$(Cys 109), $C_2$ (Cys-$SO_2H$ 112), S (Ser 113) and $C_3$ (Cys-SOH 114) coordinate to the non-heme iron. In the figure, a bound NO molecule is also represented.

Accordingly, $X_1$ to $X_6$ in the sequence represented by the general formula (1), and $X_3$ and $X_4$, in the sequence represented by the general formula (2) are suitably selected from amino acids which can bind to the non-heme iron to form the claw setting structure.

The peptide of the present invention can be obtained by, for example, enzymatical degradayion wild type NHase derived from microorganisms such as Rhodococcus sp. N-771 (FERM P-4445). First, by treating α subunit of wild type NHase with trypsin, the 24-residue peptide can be obtained. Then, by successively digesting this peptide with thermolysin, then leucine aminopeptidase and carboxypeptidase M, the objective sequence $IVC_1SLC_2SC_3TAW$ can be obtained.

Alternatively, the peptide can be produced by a publicly known genetic engineering technique based on the desired amino acid sequence.

The present invention includes a method for imparting photoreactivity to cells by introducing the aforementioned peptide sequence of the present invention into at least one protein which is involved in a metabolic system and/or energy metabolic system of the cells. By introducing the above peptide sequence of the present invention into a protein, a photoreactive non-heme iron center having the claw setting, structure shown in FIG. 3 can be formed. The present invention also includes a method for imparting photoreactivity to cells by introducing the aforementioned peptide sequence of the present invention together with a non-heme iron which is binding to the peptide into at least one protein which is involved in a metabolic system and/or energy metabolic system of the cells. The aforementioned peptide sequence of the present invention can be introduced into one or several kinds of proteins. In particular, by introducing it into several kinds of proteins, there can be obtained advantages that metabolic rates can be controlled among several pathways, and a metabolic pathway suitable for the desired production can be selectively activated.

The present invention further includes a cell having an NO producing system and photoreactivity wherein the aforementioned peptide sequence of the present invention is introduced into at least one protein which is involved in a metabolic system and/or energy metabolic system of the cell. The present invention also includes a cell having an NO producing system and photoreactivity wherein the aforementioned peptide sequence of the present invention is introduced together with a non-heme iron which is binding to the peptide (having the claw setting structure shown in FIG. 3) into at least one protein which is involved in a metabolic system and/or energy metabolic system of the cell. The peptide sequence of the above the present invention can be introduced into one or several kinds of proteins. In particular, by introducing it into several kinds of proteins, there can be obtained advantages that metabolic rates can be controlled among several pathways, and a metabolic pathway suitable for the desired production can be selectively activated.

As the protein to which photoreactivity is imparted, for example, enzymes having a mononuclear non-heme iron such as catechol dioxygenase, lipoxygenase and tyrosine hydroxylase can be mentioned. When these enzymes are used, genes for them are isolated to form a recombinant expression vector, and then a nucleotide sequence to be translated into the peptide of the present invention is introduced into a gene region for the portion around the non-heme iron binding site by a recombinant DNA technique to form a expression vector for a recombinant protein having a photoreactive non-heme iron center.

When it is desired to impart photoreactivity to a specific step of an enzymatic process involving several enzymes, imparting photoreactivity may be achieved as follows. First, a recombinant gene for a protein functioning in the step to which photoreactivity is desired to be imparted in which the photoreactive non-heme iron center is introduced is constructed by the method described above. Then, the recombinant gene is transferred into a cell having production process of a target biomolecule by using a known genetic engineering technique such as homologous recombination to impart photoreactivity to the cell. Thus, photo-control of a production process of useful biomolecule can be realized.

A source of NO supply can be introduced by constructing an expression vector for an NO synthase utilizing arginine as a substrate, and introducing it into a host concurrently with the aforementioned vector for expressing a mutant. Because the NO synthase is activated with calcium ion, inactivation by NO can be controlled by two kinds of factors, dark condition and calcium ion. Thus, a protein having photoreactivity can be prepared.

EXAMPLES

The present invention will be further explained with reference to the following examples.

EXAMPLES

All manipulations were operated in the dark to avoid photodissociation of NO from the iron center. The isolation of α subunit from NHase was performed according to the method described in J. Biochem., 119, 407–413 (1996).

The α subunit which had been isolated from inactive NHase derived from Rhodococcus sp. N-771 (FERM P-4445) was thoroughly desalted using a Centriprep-10 (Amicon) with 20 mM Tris-HCl, pH 8.0, containing 10 mM $CaCl_2$ and 2 mM 2-mercaptoethanol. The α subunit at a final concentration of 2–2.5 mg/ml in 500 µl was treated with TPCK trypsin (14 µg) for 3 hours at 37° C. The digests were subjected to reversed-phase HPLC with a Capcell pak C18 column (4.6×250 mm, Shiseido). The elution conditions were as follows. Solvent A was 20 mM Tris-HCl, pH 7.5, containing 2 mM 2-mereaptoethanol, and Solvent B was 20% A+80% acetonitrile. The content of B was increased as; 0–2 min, 0%; 2–4 min, 0–20%; 4–24 min, 20–60%; and 24–26 min, 60–100%. The flow rate was 1.0 ml/min. The eluent was monitored by a diode array detector, HEWLETT PACKARD, HP1090 Liquid Chromatography. Sequence of the product provided was determined by an amino acid sequencer. As a result, it was a single [SEQ ID NO:5] fragment composed of 24 residues of $_{105}$Asn-$_{128}$Lys [N-V-

I-V-C-S-C-T-A-W-P-I-L-G-L-P-P-T-W-Y-K]. Solvent A was changed to 5 mM ammonium acetate, pH 7.5, and reversed-phase HPLC was performed under the same condition as described above. When the amount of iron atoms bound to in the resulted peptide was determined by ICP-MS, it was found that one peptide bound one Fe atom.

Figure 2:
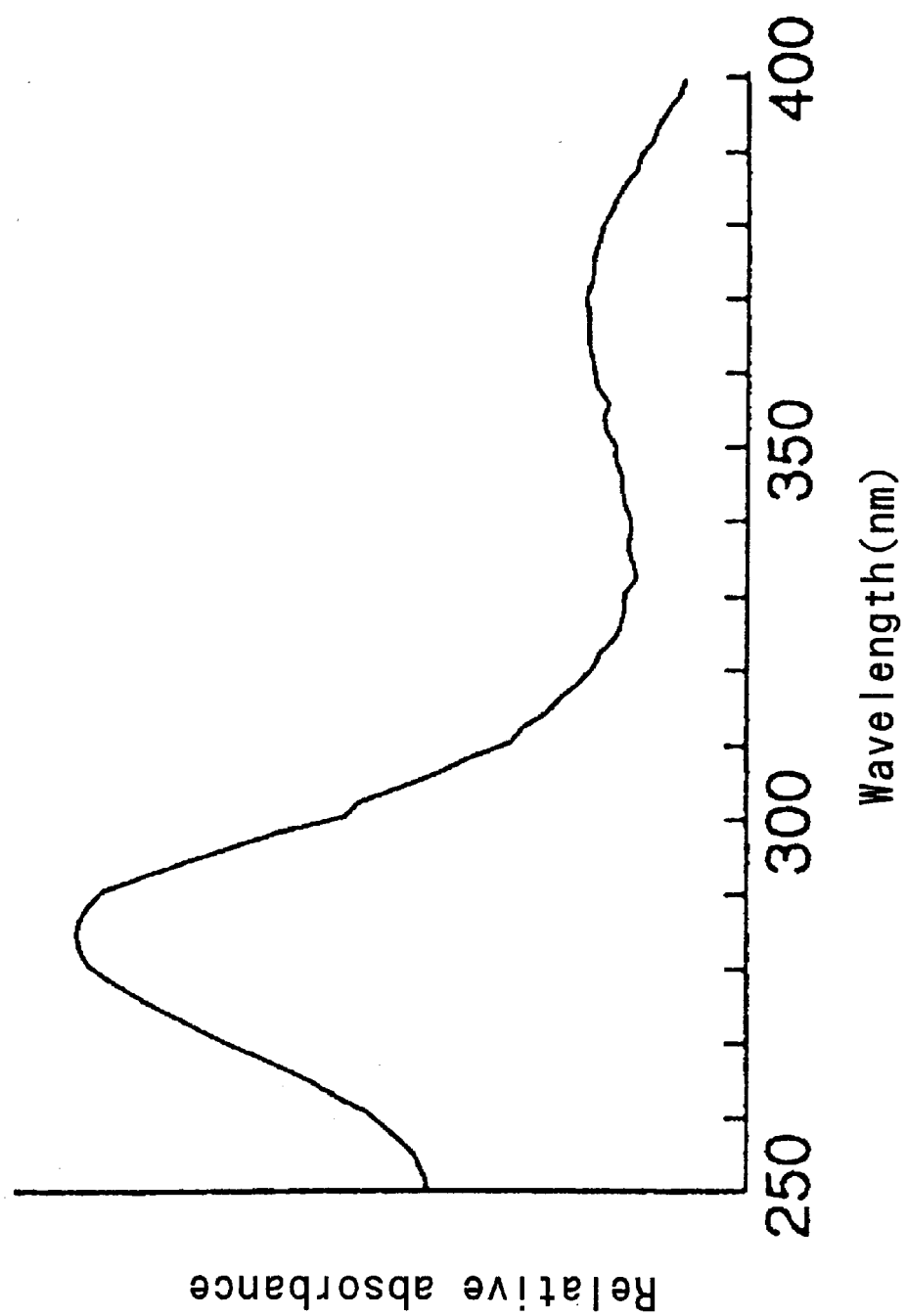
FIG. 2 is a UV absorption spectrum of a peak at retention time of 11.6 minutes in reverse phase HPLC of products from the digestion with thermolysin, carboxypeptidase-Y and leucine aminopeptidase-M.

Then, the peptide resulted above was further digested. The peptide (1.35 μg) in 20 mM Tris-HCl, pH 7.5 was treated with 1 μg of thermolysin for 1 hours at 37° C., and then with carboxypeptidase-Y (1 μg) and leucine aminopeptidase-M (1 μg) for 12 hours at 37° C. The digests were separated by reversed-phase HPLC using Capcell pak C18 column (4.6×250 mm, Shiseido). The gradient condition was as follows. Solvent C was 20 mM ammonium acetate, pH 7.5 and Solvent D was 20% Solvent C+80% acetonitrile. The column was equilibrated with 100% of Solvent C and a linear gradient was run from 0% of solvent D to 80% over a period of 20 min at a flow rate of 0.2 ml/min. The result of the reversed-phase HPLC is shown in FIG. 1, and a UV absorption spectrum of a peak at retention time of 11.6 minutes in the reversed-phase HPLC is shown in FIG. 2. In the UV absorption spectrum of the peak at retention time of 11.6 minutes, an absorption peak at 370 nm was observed, and it indicates that the contained fragment was associated with a nitrosylated iron. In a photo-irradiated peptide, the aforementioned absorption peak at 370 nm completely disappeared.

Sequence of the resulted product was determined by an amino acid sequencer. As a result, it was a single fragment [SEQ ID NO.:6] composed of 11 residues of $_{107}$I-V-S-L-C-S-C-T-A-$_{117}$W.

Existence of Post-translational Modification

Cysteine residues cannot be detected when sequencing was performed with an amino acid sequencer. The aforementioned 24-residue peptide of $_{105}$N to $_{128}$K ($_{105}$NVIVCSLCSCTAWPILGLPPTWYK$_{128}$) contains three cysteine residues, and the remaining 21 residues have already been identified. Therefore, also considering the result of the mass spectrometry, the peptide fragment provided from trypsin digestion was subjected to carboxymethylation after reduction to alkylate the cysteine residues, and then the analysis by the amino acid sequencer was attempted. As a result, among the cysteine cluster containing three cysteines ($_{109}$C-S-L-$_{112}$CS-$_{114}$C), the 112nd cysteine still could not be detected as before, whereas the 109th and the 114th cysteines could be detected as carboxymethylcysteines. At the same time, mass of this sample was measured by using MALDI-TOF MS (matrix-assisted laser desorption ionization time of flight mass spectrometer) as a mass spectrometer. As to the mass number, in addition to the molecular weight of $_{105}$N to $_{128}$K (2663.3), increment considered to be due to binding of two carboxymethyls (molecular weight: 59) and further increment of 32 Da were detected.

Identification of Cysteinesulfinic Acid

From the results of mass spectrometry and amino acid sequencing, it became clear that modification of 32 Da increment occurred at the 112nd cysteine. It is assumed that sulfur (32) or oxygen-molecule (16×2) corresponds to the mass number of 32. However, if it was due to sulfur atom (Cys-S$_2$H), it should be carboxymethylated after reduction. Therefore, the most probable modification was considered to be oxidation by two oxygen atoms. The present inventors considered that the cysteine residue is present in the fragment as cysteinesulfinic acid (Cys-SO$_2$H), which corresponds to cysteine residue oxidized by two oxygen atoms, and identified it by amino acid analysis as follows. Amino acid composition analysis was performed by the method established by Hayashi et al. wherein antipodes of amino acids are derivated with a fluorescent reagent, (+)-1-(9-fluorenyl)ethyl chloroformate (FLEC), and separated by reversed-phase chromatography (Hayashi et al., 1993).

In order to prevent the oxidation of cysteine residue, hydrolysis of the peptide was performed with an enzyme (leucine aminopeptidase). However, since the 112nd amino acid is the eighth amino acid residue from the N-terminus of the peptide, and yield will be decreased as it is more remote from the N-terminus, the fragment was preliminarily subjected to secondary digestion with thermolysin. The resulting digestion mixture was purified by reversed-phase chromatography to afford several fragments, and a fragment of the objective 8 residues of from 111st leucine to 118th proline ($_{111}$L-X-S-CM-T-A-W-$_{118}$P wherein X is a residue considered to be cysteinesulfinic acid, and CM is carboxymethylcysteine) was eluted at 7.8 min.

The molecular mass of the fragment obtained by the above secondary digestion was estimated by MALDI-TOF MS, and detected as 970.7, which was larger than the theoretical molecular weight of 938.1 by 32 Da. That is, the modification of 32 Da increment still remained in this fragment. Then, it was hydrolyzed into individual amino acids with leucine aminopeptidase to perform amino acid composition analysis. As controls, D,L-cysteic acid and L-cysteinesulfinic acid were analyzed, and respective elution time was 22.9 min (L-cysteic acid), 23.4 min (D-cysteic acid), and 26.7 min. From the area values of the peaks, it was considered that about 39% of sulfinic acid was oxidized to cysteic acid in this measurement.

In the amino acid composition analysis of the peptide of 8 residues obtained from the secondary digestion with thermolysin, peaks were detected at elution times of 22.7 min and 26.2 min. From the ratio of the area values, it was thought that about 56% of the residue was converted into cysteic acid. The yield of leucine of the N-terminus of this fragment was 97.3 pmol, whereas the yield of cysteinesulfinic acid including those oxidized into cysteic acid was 99.0 pmol (cysteinesulfinic acid: 44 pmol, cysteic acid: 55 pmol).

From the results mentioned above, it has been revealed that the 112nd cysteine residue in the above peptide fragment was modified by oxidation with two oxygen atoms into cysteinesulfinic acid (Cys-SO$_2$H).

Structure Determination of the Nitrosylated NHase

Figure 4:
FIG. 4 shows a hetero-tetramer structure $((\alpha\beta)_2)$ in an asymmetric unit.
Figure 4:

The crystal of the nitrosylated NHase (inactive NHase) diffracted X-ray up to high resolution, 1.7 Å resolution, and belonged to the space group of P2$_1$2$_1$2 with cell dimensions of a=117.4 Å, b=145.6 Å and c=52.1 Å. Two αβ heterodimers existed in an asymmetric unit of the crystal. The crystal structure of the inactive NHase was determined by multiple isomorphous replacement (MIR) analysis followed by density modification and non-crystallographic symmetry averaging. The structural model was crystallographically refined at 1.7 Å resolution (R-factor 0.179, R-$_{free}$0.228). FIG. 4 shows a hetero-tetramer structure ((αβ)$_2$) in an asymmetric unit. The folding pattern of the inactive NHase is very similar to that of the photoactivated enzyme, showing that the conformation is conserved between the inactive and photoactivated enzymes. While the inactive NHase formed a hetero-tetramer in the crystal, sedimentation equilibrium and dynamical light scattering measurements showed that the enzyme existed in a dimer-tetramer equilibrium in solution depending on its concentration. The non-heme iron center was located at the interface between the two subunits in the hetero-dimer.

Structure of the Active Center

Figure 5:
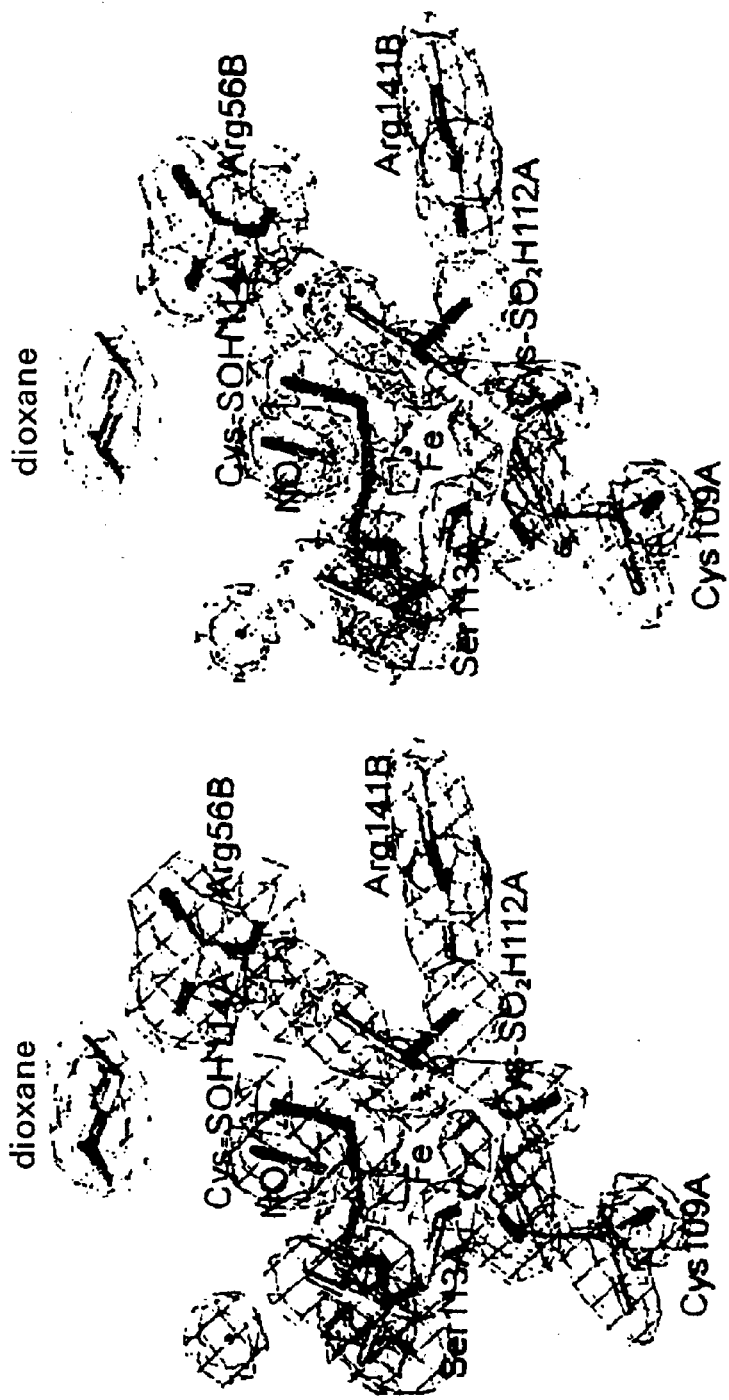
FIG. 5 shows omit-annealed Fo-Fc maps of an active site region.

FIG. 5 shows the omit-annealed Fo-Fc maps of the active site region. Each residue was clearly resolved. The active site was composed of four amino acid residues from the α subunit ($\alpha Cys^{109}$, $\alpha Cys^{112}$, $\alpha Ser^{113}$, $\alpha Cys^{114}$) and two amino acid residues from the β subunit ($\beta Arg^{56}$, $\beta Arg^{141}$). The ligands to the non-heme iron atom are sulfur atoms of the three cysteine residues ($\alpha Cys^{109}$, $\alpha Cys^{112}$, $\alpha Cys^{114}$), main chain amide nitrogen atoms ($\alpha Ser^{113}$, $\alpha Cys^{114}$) and nitric oxide (NO). Only the site occupied by nitric oxide is accessible from solvent. The atoms coordinating to the iron of the inactive type were identical to those in the photoactivated one except for the nitrogen of nitric oxide. The two sulfur atoms (S γ atoms of $\alpha Cys^{112}$ and $\alpha Cys^{114}$), the two amide nitrogen atoms and the iron atom were arranged in the same plane. The length of the Fe—N(NO) bond in the inactive NHase was 1.65 Å, which was comparable to those in many nitrosyl iron(III) complexes. The nitric oxide coordinated with the non-heme iron(II) in a bent configuration with a Fe—N—O angle of 158.6° tilted toward the middle of $\alpha Cys^{112}$ and a $Cys^{114}$.

Post-translational Modifications in the Active Center

Figure 7:
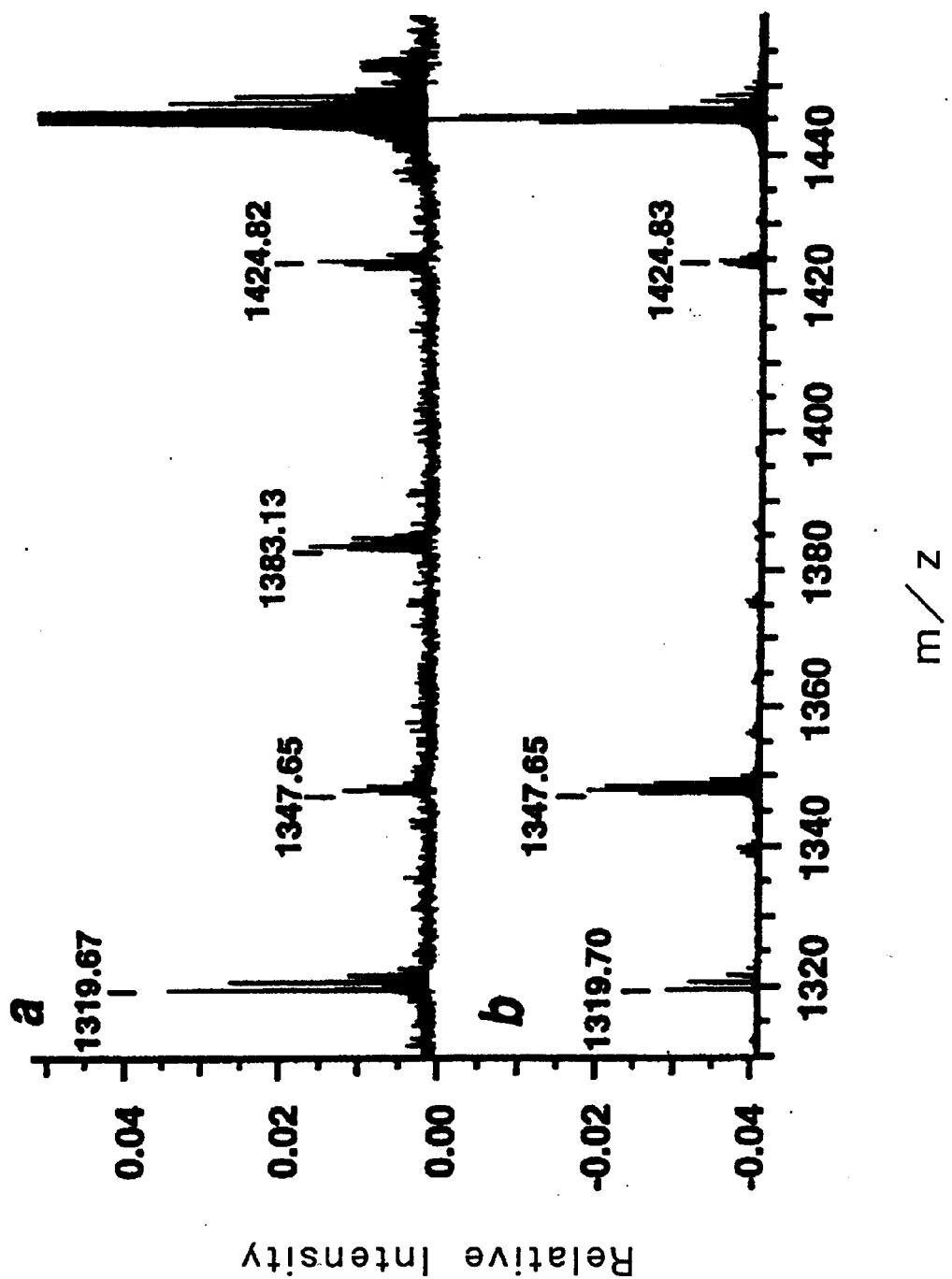
FIG. 7 shows an electrospray mass spectrum.

General structure of the active center can be seen in the omit-annealed Fo-Fc maps. Extra electron densities appeared around the Sγ atoms of a $Cys^{112}$ and α $Cys^{114}$ (FIG. 5). Since $\alpha Cys^{112}$ is post-translationally modified to a cysteinesulfinic acid ($Cys-SO_2H$), the two additional electron densities around S γ of $\alpha Cys^{112}$ is thought to correspond to the two oxygen atoms of the sulfinyl group. It was assumed that $\alpha Cys^{114}$ was also post-translationally modified, because there was no atom to ascribe the additional electron density close to Sγ of $\alpha Cys^{114}$ in any known models. To confirm this idea, the tryptic digests of the inactive NHase were examined by FT-ICR MS. FIG. 7a shows the positive electrospray ionization mass spectra of a tryptic digest of inactive NHase α subunit in the neutral condition. Two signals with m/z of 1347.65 and 1383.13 were assigned for doubly charged, $(M+2H)^{2+}$, iron center peptides ($\alpha Asn^{105}$-$\alpha Lys^{128}$) without and with $Fe^{3+}$, respectively. The former contained α $Cys^{109}$-S-S-$\alpha Cys^{114}$ and $\alpha Cys^{112}$-$SO_2H$ ($M_r$, =2693.31), and the latter contained α $Cys^{109}$-$S^-$, $\alpha Cys^{114}$-$SO^-$ and $\alpha Cys^{112}$-$SO^{2-}$ (M'2764.23). Assuming no post-translational modification occurred on $\alpha Cys^{114}$, expected $M_r$ of the latter (2748.24) was smaller by 16.02 than the observed value. Upon addition of acetic acid, the latter signal disappeared and the relative intensity of the former, was doubled or more (FIG. 7b). In the acidic condition, the peptide released $Fe^{3+}$, which was replaced by 3 protons, and a disulfide bond was formed between αCys-$SOH^{114}$ and αCys-$SH^{109}$ as a result a water molecule is produced. The measured mass difference of two signals (35.48×2=70.96) was well in accord with the calculated difference (55.93−3.03+18.01=70.92). Thus, we concluded that $\alpha Cys^{114}$ is modified to Cys-SOH, and the additional electron density corresponds to the oxygen atom of the sulfenyl group. It is considered that, since acidic condition was used for the experiment on cysteinesulfenic acid, the presence of acid-labile cysteinesulfenic acid was overlooked.

Stabilization of Nitric Oxide by "the Claw Setting"

Figure 6:
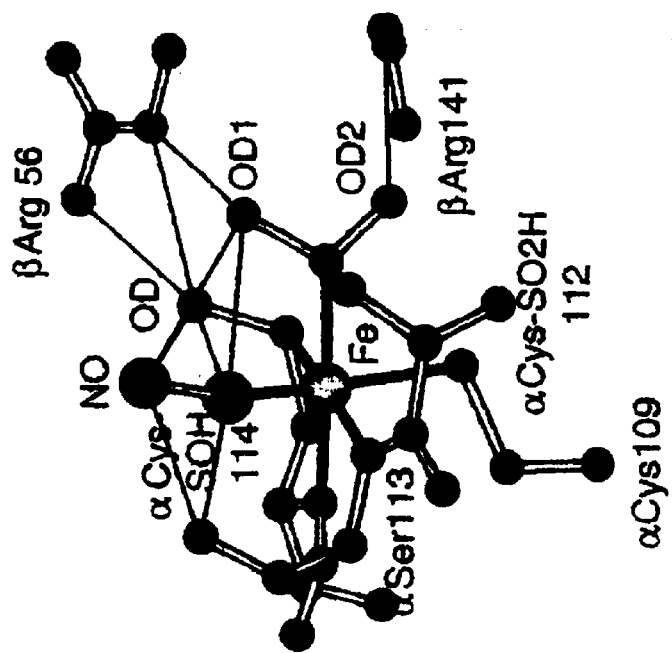
FIG. 6 shows a claw setting structure formed by a peptide $C_1SLC_2SC_3$ binding to a non-heme iron.
Figure 6:
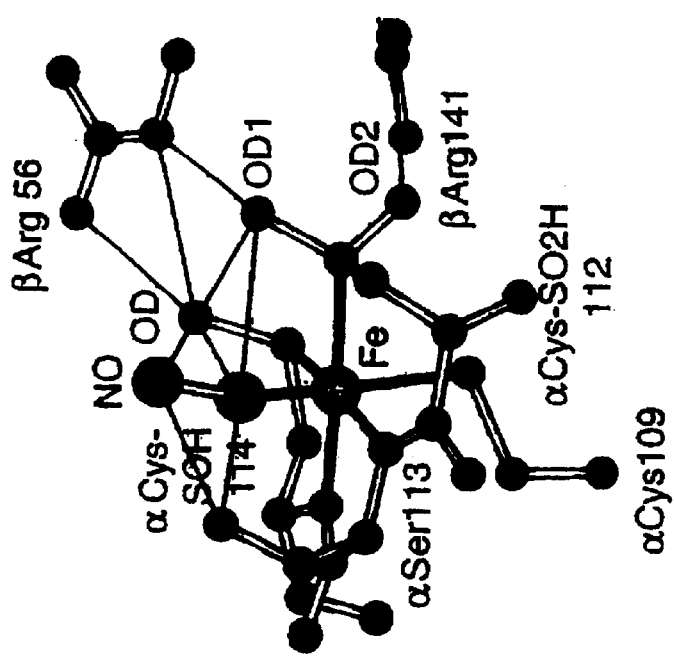

As shown in FIG. 6, three oxygen atoms, O δ1 of $\alpha Cys-SO_2H^{112}$O δ of α $Cys-SOH^{114}$ and O γ of $\alpha Ser^{113}$, were protruded from the plane containing the iron atom by 1.5 Å like claws (of rings), and a nitric oxide molecule was held at the center of the three "claws". This structure is named as "claw setting". These three oxygen atoms are located at a distance from the nitric oxide molecule close enough to have strong interaction within them. The nitrosyl iron complex of the NHase, whose iron exists in a low-spin ferric(II) state as indicated by ESR studies, is stable more than one year under aerobic condition as long as shielded from light. Moreover, the nitrosylated iron center is stable even in a proteolytic fragment from $\alpha Ile^{107}$ to a $Trp^{117}$, whereas the association constant of nitric oxide to ferric(III) irons are much smaller than those to ferrous(II) ones in hemeproteins, and the association is generally unstable in air. The extraordinary stability of the nitrosyl non-hem ferric(III) iron center in NHase having iron(III) is likely to be due to the interaction between the nitric oxide and the oxygen atoms in the "claw setting". On the contrary, the nitric oxide immediately dissociates from NHase after light irradiation. Fourier transform infrared difference spectrum showed that a local structural change occurs around the iron center upon light irradiation. These results suggest that light irradiation breaks the Fe—N(NO) bond, and thus weakens the interaction between the oxygen atoms and the nitric oxide which induces the structural change of the "claw setting". Taken together, the photoreactivity of Fe-type NHase is likely to be explained in terms of the "claw setting".

$\alpha Cys-SO_2H^{112}$ and $\alpha Cys-SOH^{114}$ were stabilized by hydrogen bonds formed with $\beta Arg^{56}$ and $\beta Arg^{141}$ (FIG. 6). These arginine residues are conserved in all known NHases. The replacement of these residues with other amino acids resulted in the loss of activity, and induced a significant change in the absorption spectra reflecting the electronic state of the catalytic center (M. Tsujimura et al.). This fact suggests that the "claw setting" is also important for the enzymatic activity of NHase.

According to the present invention, there can be provided a peptide with a shorter peptide chain capable of imparting photoreactivity, which can be easily introduced into a protein with a little risk in degrading original function of the protein. It is also be possible to impart photoreactivity to a cell by utilizing this peptide. As a result, it becomes possible to control production of a great number of useful biomolecules such as amino acids, peptides, proteins, carbohydrates, and lipids by presence and absence of light irradiation.

What is claimed is:

1. A peptide consisting of the amino acid sequence of formula (1):

$$X_1X_2C_1X_3X_4C_2SC_3X_5X_6X_7 \quad (1)$$

wherein $X_1$ to $X_7$ are any amino acid, $C_1$ is cysteine, $C_2$ is cysteinesulfinic acid, $C_3$ is cysteinesulfenic acid, and S is serine.

2. A peptide according to claim 1 wherein the sequence of formula (1) is $$IVC_1SLC_2SC_3TAW$$

wherein I is isoleucine, V is valine, $C_1$ is cysteine, $C_2$ is cysteinesulfenic acid, $C_3$ is cysteiesulfenic acid, S is serine, L is leucine, T is threonin, A is alanine, and W is tryptophan.

3. A peptide according to claim 1, which forms a claw setting structure by binding to a non-heme iron.

* * * * *